United States Patent [19]

Hanazato et al.

[11] Patent Number: 4,894,339

[45] Date of Patent: Jan. 16, 1990

[54] IMMOBILIZED ENZYME MEMBRANE FOR A SEMICONDUCTOR SENSOR

[75] Inventors: Yoshio Hanazato; Satoru Shiono; Mamiko Nakako; Satoshi Yamada, all of Hon, Japan

[73] Assignee: Seitaikinouriyou Kagakuhin Sinseizogijutsu Kenkyu Kumiai, Japan

[21] Appl. No.: 942,797

[22] Filed: Dec. 17, 1986

[30] Foreign Application Priority Data

Dec. 18, 1985 [JP] Japan ................................ 60-283056
Jan. 27, 1986 [JP] Japan ................................ 61-13900
Jan. 27, 1986 [JP] Japan ................................ 61-13902

[51] Int. Cl.$^4$ ...................... C12N 11/04; C12N 11/08; C12M 1/40; G01N 27/26
[52] U.S. Cl. ..................................... 435/182; 204/403; 435/180; 435/288; 435/817
[58] Field of Search ............... 435/174, 177, 180, 182, 435/817, 288; 204/403

[56] References Cited

U.S. PATENT DOCUMENTS

| | | | |
|---|---|---|---|
| 4,160,698 | 7/1979 | Miyairi et al. | 435/180 X |
| 4,269,941 | 5/1981 | Ichimura | 435/180 X |
| 4,464,468 | 8/1984 | Arrameas et al. | 435/182 X |
| 4,476,005 | 10/1984 | Tokinaga et al. | 435/177 X |
| 4,631,249 | 12/1986 | Kalyanaraman | 430/167 X |

OTHER PUBLICATIONS

Chemical Abstracts, vol. 103, No. 19, Nov. 11, 1985, p. 371, Abstract No. 156849q (Japanese Patent Document No. 60-79258).
"The Application of Chemiluminescence of a Cypridina Luciferin Analog to Immobilized Enzyme Sensors", Agricultural and Biological Chemistry, vol. 45, No. 6, Jun. 1981, pp. 1403–1408.
"Application of Water Soluble Photo-Crosslinkable Polymer to Enzyme Membrane for FET-Biosensor", Proceedings of the Second International Meeting on Chemical Sensors, Bordeaux, France, Aucouturier, editor, pp. 576–579 (Jul. 7–10, 1986) Hanazato et al.
"Glucose Sensor Based on a Field-Effect Transistor with a Photolithographically Patterned Glucose Oxidase Membrane", Analytica Chimica Acta, 193 pp. 87–96 (1987), Hanazato et al.
"Formation of an Enzyme Immobilized Membrane...", Shimoide et al, Denki Gakkai Kenkyuukai Shiryou (Electric Society Research Material) (EIM-85-48 to 56, EFM-85-27 to 35), May, 1985.
"Investigation on A Semiconductor Enzyme Sensor...", Y. Hanazato, Preprint for Japanese Chemical Society 1985 Spring Meeting.
"Bioelectrode Using Two Hydrogen Ion Sensitive Field Effect ...", Proceedings of the International Meeting on Chemical Sensors, pp. 513–518 (1983).

Primary Examiner—David M. Naff
Attorney, Agent, or Firm—Leydig, Voit & Mayer

[57] ABSTRACT

A membrane containing an immobilized enzyme for a semiconductor sensor is prepared containing a water soluble photosensitive resin including a high molecular weight polyvinyl pyrrolidone crosslinked to 2, 5-bis (4'-azide-2'-sulfobenzal) cyclopentanone sodium salt, and an enzyme. Glutaraldehyde and bovine serum albumin, polyamino acid or polyamino amino acid copolymer may also be present to provide chemical crosslinking. The enzyme may be glucose oxidase, urease or lipase. The membrane can be directly formed on ion-sensitive protions of a pH-ion sensitive field effect transistor to form a semiconductor sensor by coating an aqueous solution of the resin and enzyme on the ion-sensitive portion, drying and irradiating with light such as ultraviolet light to provide photo crosslinking.

56 Claims, 9 Drawing Sheets

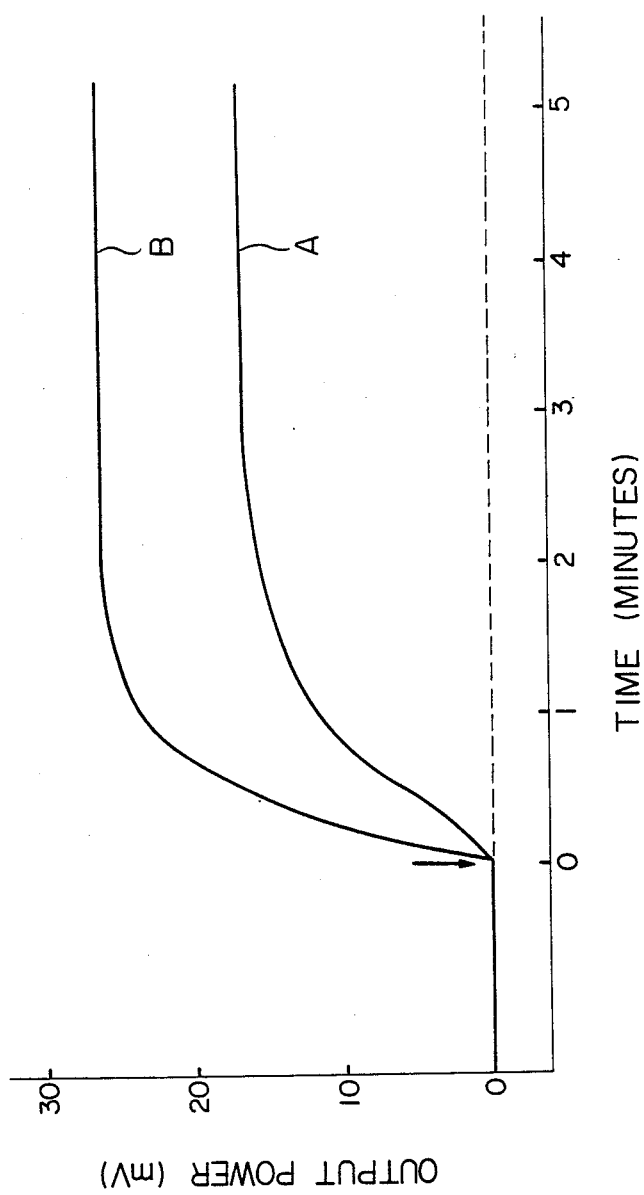

IMMOBILIZED ENZYME MEMBRANE FOR A SEMICONDUCTOR SENSOR

BACKGROUND OF THE INVENTION

1. Field of the Invention

The present invention relates generally to enzyme immobilized membranes and a method for producing the same, and more specifically, to a semiconductor enzyme sensor utilizing such enzyme immobilized membranes.

2. Description of the Prior Art

In the past, enzymes have been industrially utilized as catalysts, particularly in the fermentation industry, and the like. In general, enzymes were dissolved or dispersed in aqueous solutions for promoting various chemical reactions and, after completion of the reactions, the enzymes were not recovered from the solutions but discarded uselessly each time the respective reactions had been finished. In recent years, however, enzyme immobilization techniques have been developed which enable repeated use of enzyme in a stable state, whereby areas of utilization of enzymes have been rapidly expanded, for example, to a field of measuring various parameters of chemical substances in addition to traditional fields of fermentation, syntheses of chemical substances, and the like.

The measurements of concentrations of respective components contained in body fluids such as blood or urine are very important for clinical diagnosis and thus there have been developments and/or improvements made of various kinds of quantitative measurements. Of these, many enzyme sensors have been proposed which are able to effect quick and continuous measurements by employing enzyme immobilized membranes and varying kinds of electrodes.

Such enzyme sensors have been studied since about 1970 and today it becomes possible to measure chemical and physical quantities of a wide variety of substances by the use of enzyme sensors.

In the enzyme sensors fabricated in the early years, an enzyme immobilized membrane was physically or chemically adhered to a sensitive portion of an enzyme sensor which is adapted to convert physical or chemical quantities such as temperature, ion concentration, gas concentration or the like into electrical signals. In these days, however, in accordance with miniaturization and/or multiplication of enzyme sensors, it becomes necessary to selectively form an enzyme immobilized membrane on a limited area of a sensitive portion of a sensor.

In order to measure chemical quantities of a substance, an enzyme immobilized membrane is suitable which has a thin thickness and a limited area.

Biosensors are typical examples of sensors utilizing enzyme immobilized membranes for measurements of chemical substances. Such a biosensor comprises an enzyme immobilized membrane, and a transducer adapted to detect substances consumed or produced in the membrane and generate electrical signals upon detection of such substances. In this case, the enzyme immobilized membrane serves to discriminate a specific chemical substance to be measured, and cause a change in quantity of a material which corresponds to a change in the chemical substance and which is able to be detected by the transducer.

Among such biosensors, there are known those which employ a combination of a glucose immobilized membrane and an oxygen electrode, a combination of a glucoseoxidase immobilized membrane and a hydrogen peroxide electrode, a combination of glucoseoxidase immobilized membrane and a pH electrode, or the like. Glucose oxidase acts to decompose the glucose in the presence of oxygen in an enzyme immobilized membrane into gluconic acid and hydrogen peroxide according to the following reaction equation:

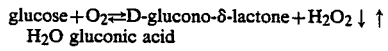

Accordingly, it is possible to measure the concentration of glucose by detecting the quantity of oxygen consumed in the above reaction with the oxygen electrode, the quantity of hydrogen peroxide produced in the above reaction with the hydrogen peroxide electrode, and a reduction of pH due to production of gluconic acid with the pH electrode.

Further, in order to form an enzyme immobilized membrane as employed in a miniaturized or multiplicated enzyme sensor as referred to above, a water soluble photosensitive resin such as, for example, photosensitive polyvinyl alcohol (PVA) is subject to a photolithographic process. FIGS. 1A through 1C show a series of procedures in a conventional method for forming an enzyme immobilized membrane from a photosensitive resin by means of photolithography. In these figures, reference numeral 1 designates a base or substrate such as, for example, a silicon wafer having a thermally grown oxidized film or membrane, a base board having amino groups introduced therein through a silane coupling agent, a transducer, a semiconductor sensor or the like. Provided on the entire surface of the substrate 1 by spin coating is an enzyme membrane 3 formed of a water soluble photosensitive resin containing an enzyme 2 such as glucose oxidase dissolved therein, as illustrated in FIG. 1A. Then, the enzyme membrane 3 thus formed is irradiated by ultraviolet light or visible light 6 through an appropriate photomask or filter 5 so that only a specific portion 4 of the enzyme membrane 3 or a sensitive portion 4 of the substrate 1 is subject to the irradiation of the light to provide photo crosslinking therein (see FIG. 1B). Thereafter, the remaining portion of the enzyme membrane 3, not irradiated by the light 6 and having no photo crosslinking, is developed and washed with water (see FIG. 1C).

With the above-described conventional method for forming an enzyme immobilized membrane, there arise the following problems due to the water development carried out after formation of photo crosslinking. Specifically, the specific portion having photo crosslinking is liable to be peeled off during the water development, and does not have sufficient mechanical strength for use in an aqueous solution; and the enzyme immobilized in the enzyme membrane 3 is liable to elute therefrom. Such phenomena become more remarkable as the amount of enzyme in the enzyme membrane 3 increases.

As a result, it is difficult to produce a highly sensitive biosensor in accordance with the conventional method for forming an enzyme immobilized membrane.

In general, there is another conventional method for making an enzyme immobilized membrane in an enzyme sensor for measuring glucose in which crosslinking is formed between glucose oxidase and bovine serum albumin by means of glutaraldehyde. FIG. 2 is an imaginary view showing a glucose-oxidase immobilized membrane formed on a base or transducer 1 having amino groups introduced thereinto by a silane coupling agent.

In the above glucose oxidase immobilized membrane forming method, an enzyme 2 in the form of glucose oxidase and bovine serum albumin 7 are dissolved in an aqueous solution, and then mixed with a solution containing an appropriate concentration of glutaraldehyde 8. The mixture thus formed is coated on the base 1 and kept in this state so that chemical crosslinking is produced between enzyme 2-enzyme 2, enzyme 2-bovine serum albumin 7, bovine serum albumin 7- bovine serum albumin 7, and enzyme 2-amino groups on the surface of the base 1, bovine serum albumin 7- amino groups on the base surface under the action of glutaraldehyde. In this manner, the enzyme 2 is captured in a three-dimensional polymer membrane, as illustrated in FIG. 2, and thus becomes insoluble in water and immobilized.

With recent enzyme sensors, there is a strong need for miniaturization and hence finely machinable materials and production methods therefore are required for such glucose oxidase immobilized membranes. The conventional glucose oxidase immobilized membranes are produced from the above-mentioned chemically crosslinked materials in accordance with the above bovine serum albumin-glutaraldehyde method, but involve a problem in that it is impossible to form enzyme immobilized membranes having limited areas with good reproducibility.

SUMMARY OF THE INVENTION

Accordingly, the present invention is intended to solve the above-described problems of the prior art.

A primary object of the present invention is to provide a novel and improved glucose oxidase immobilized membrane and a method for producing the same in which the portion of an enzyme membrane having photo-crosslinking, even if containing an excessive amount of an enzyme to raise the senor sensitivity, does not peel off from a sensitive portion of an enzyme transducer, and in which elution of the enzyme from the enzyme membrane can be effectively prevented, and in which an enzyme immobilized membrane having a limited area and high mechanical strength can be produced with good reproducibility.

Another object of the present invention is to provide a novel and improved semiconductor enzyme sensor and a method for producing the same in which an enzyme immobilized membrane can be directly formed on an ion-sensitive surface of a hydrogen ion-sensitive field effect transistor (hereinafter referred to as pH-ISFET), thereby making it easy to miniaturize the entire sensor, and which can be manufactured in an easy and efficient manner, and which has high sensitivity.

A further object of the present invention is to provide a novel and improved semiconductor enzyme sensor and a method for producing the same in which a plurality of enzyme immobilized membranes can be directly formed on the respective ion-sensitive surfaces of plural a pH-ISFET chip having plural pH-ISFET elements, thereby making it easy to produce a multiple-enzyme sensor in a simple way, and which has high sensitivity.

In order to achieve the above objects, according to one aspect of the present invention, there is provided an enzyme immobilized membrane comprising:

a water soluble photosensitive resin including polyvinyl pyrrolidone having a high molecular weight, such as a molecular weight of tens of thousands to hundred of thousands, and 2, 5-bis (4'-azide-2'-sulfobenzal) cyclopentanone sodium salt; and an enzyme.

The enzyme immobilized membrane is particularly useful in cases where it contains a limited amount of enzyme. On the other hand, when the amount of enzyme contained in the enzyme immobilized membrane is relatively great, it is preferable that the enzyme immobilized membrane further comprise glutaraldehyde, and a material adapted to cooperate with glutaraldehyde to form chemical crosslinking for improved mechanical strength.

Preferably, the enzyme is selected from the group consisting of glucose oxidase, urease and lipase.

Preferably, the material adapted to cooperate with glutaraldehyde to form chemical crosslinking is selected from the group consisting of bovine serum albumin, polyamino acid, and polyamino acid copolymer.

In a preferred embodiment, the polyvinyl pyrrolidone having a molecular weight of tens of thousands to hundred of thousands is 2-20 weight %; and the 2, 5-bis (4'-azide-2'-sulfobenzal) cyclopentanone sodium salt is 0.5-1.5 weight %; and the enzyme comprises glucose oxidase of 5.0-7.5 weight %. Also, the enzyme immobilized membrane further comprises bovine serum albumin of 5-10 weight %.

According to another aspect of the present invention, there is provided a method for producing an enzyme immobilized membrane which comprises the steps of:

coating on a base an aqueous solution which is composed of a water soluble photosensitive resin including polyvinyl pyrrolidone having a molecular weight of tens of thousands to hundreds of thousands and 2, 5-bis (4'-azide-2'-sulfobenzal) cyclopentanone sodium salt, and an enzyme;

drying the aqueous solution thus coated on the base so as to form an enzyme immobilized membrane; and irradiating ultraviolet light on the enzyme immobilized membrane to provide photo-crosslinking between the polyvinyl pyrrolidone, the cyclopentanone sodium salt, and the enzyme.

The enzyme immobilized membrane, after having been irradiated by the ultraviolet light, may be dipped into an aqueous solution of glutaraldehyde so as to form chemical crosslinking. As a result, proteins in the enzyme immobilized membrane are chemically crosslinked with each other under the action of glutaraldehyde whereby the mechanical strength of the enzyme immobilized membrane is markedly increased, thus preventing elution of the enzyme.

Preferably, the glucose oxidase immobilized membrane is washed away by a buffer solution, dipped into an aqueous solution of glycine, and again washed by a buffer solution for removal of the residual glutaraldehyde.

According to a further aspect of the present invention, there is provided a semiconductor enzyme sensor comprising:

a first pH-ISFET having a first enzyme immobilized membrane deposited thereon, the first membrane being composed of a first water soluble photosensitive resin including polyvinyl pyrrolidone having a molecular weight of tens of thousands of hundreds of thousands and 2, 5-bis (4'-azide-2'-sulfobenzal) cyclopentanone sodium salt, and a first enzyme;

a second pH-ISFET; and a reference electrode.

In a further preferred embodiment, the semiconductor enzyme sensor may further comprise a third pH-ISFET having a second enzyme immobilized membrane deposited thereon, the second membrane being composed of a second water soluble photosensitive resin including polyvinyl pyrrolidone having a molecular weight of tens of thousands to hundreds of thousands and 2, 5-bis (4'-azide-2'-sulfobenzal) cyclopentanone sodium salt, and a second enzyme.

The first and/or second enzyme immobilized membrane may be directly coated and hardened on the respective pH-ISFETs so that it becomes easy to miniaturize and manufacture the entire semiconductor enzyme sensor. In addition, the sensor thus formed has an extended satisfactory life in service. Specifically, the above photosensitive resin is by far durable against $H_2O_2$ which necessarily results as a by-product during glucose oxidation by glucose oxidase, as compared with conventional photosensitive resins such as PVA. Moreover, the above photosensitive resin is easy to synthesize or prepare, able to have a great amount of enzyme dissolved therein, highly sensitive, and can provide an enzyme immobilized membrane at low costs. On the other hand, PVA conventionally used is sensitive to lights of relatively long wavelength so that when a mask is fitted to a covering layer of PVA before being subjected to exposure, such a PVA covering layer often causes partial crosslinking. To prevent this, an exposure device is required to take special precautions. In contrast, the photosensitive resin of the present invention requires no such measure or any other adjustments.

Preferably, each of the first and second enzyme immobilized membranes are formed by coating on a pH-ISFET an aqueous solution containing a water soluble photosensitive resin, glucose oxidase, bovine serum albumin, and hardening the aqueous solution thus coated by irradiation with ultraviolet light. These enzyme immobilized membranes may be dipped into a glutaraldehyde solution to form chemical crosslinking for improved mechanical strength.

It is preferable that the first and second enzyme immobilized membranes be formed through patterning on the ion-sensitive surfaces of the respective pH-ISFETs by means of photolithography. In this case, each of the enzyme immobilized membranes can be readily and efficiently deposited through a water soluble photosensitive resin on only the specific ion-sensitive surface as required of each pH-ISFET which can be very limited in size (for example, several mm in length and width). Thus, a multiple enzyme sensor having a plurality of sensing portions which are sensitive to a plurality of different substances can be obtained in an easy and efficient manner. This multiple sensor is independently usable by itself, or can be formed into an intelligent sensor which has an information processing circuit adapted to receive outputs of the various sensing portions for making comprehensive judgement.

The semiconductor enzyme sensor may further include one or more pH-ISFETs each having a further enzyme immobilized membrane deposited thereon. In this case, the further membrane is preferably composed of a further water soluble photosensitive resin including polyvinyl pyrrolidone having a molecular weight of tens of thousands to hundreds of thousands and 2, 5-bis (4'-azide-2'-sulfobenzal) cyclopentanone sodium salt, and a further enzyme.

The above and other objects, features and advantages of the present invention will become apparent from the following detailed description of several presently preferred embodiments of the invention when taken in conjunction with the accompanying drawings.

BRIEF DESCRIPTION OF THE DRAWINGS

FIG. 12 is a graphic representation showing changes in output power of multiple enzyme sensors of the invention over time.

DESCRIPTION OF THE PREFERRED EMBODIMENTS

Figure 1A:
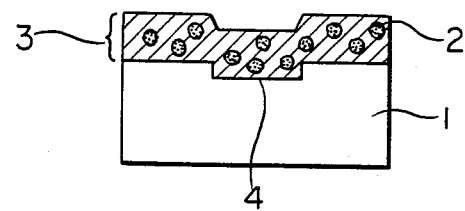
FIGS. 1A, 1B and 1C are cross sectional views of a conventional semiconductor enzyme sensor, respectively showing a series of processes in accordance with a conventional method for producing an enzyme immobilized membrane.
Figure 1B:
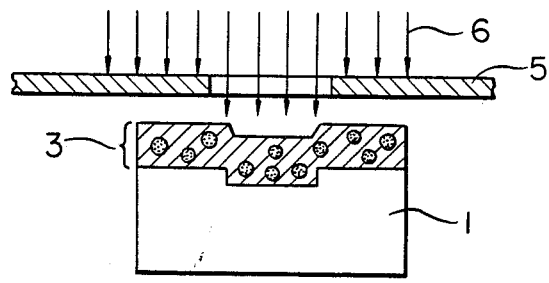
Figure 1C:
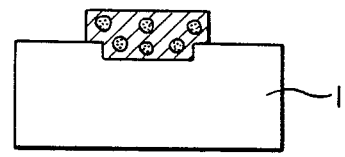
Figure 2:
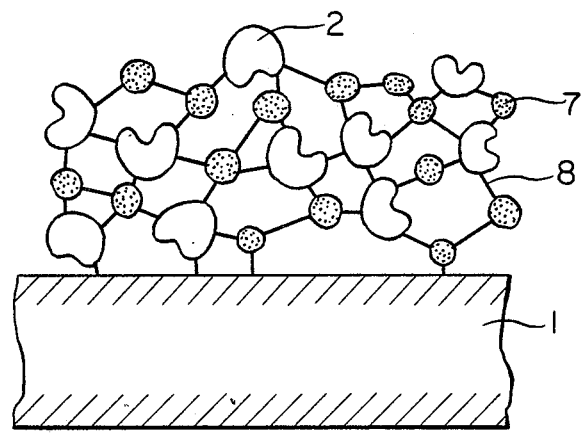
FIG. 2 is a schematic view showing a conventional glucose oxidase immobilized membrane formed on a base.

The present invention will now be described in detail with reference to the accompanying drawings. In the following description and the accompanying drawings, the same or corresponding components or elements in the illustrated embodiments of the invention are identified by the same reference numerals.

Figure 3A:
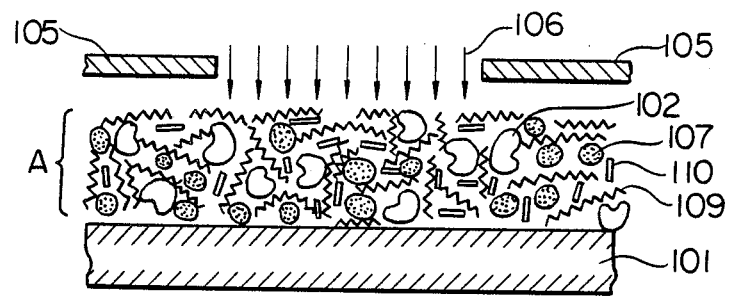
FIGS. 3A, 3B and 3C are schematic views showing a series of processes in accordance with a method of the invention for producing a glucose oxidase immobilized membrane.
Figure 3B:
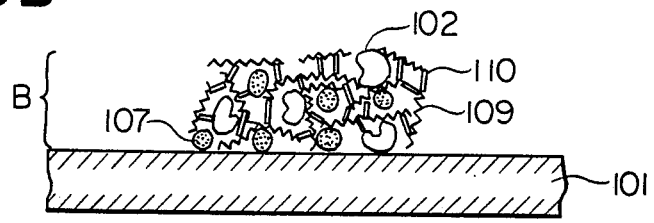
Figure 3C:
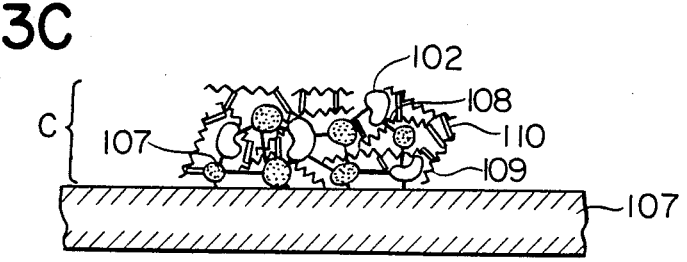

FIGS. 3A, 3B and 3C schematically illustrate a series of processes in a method for producing enzyme immobilized membranes according to the present invention. In these figures, the enzyme immobilized membrane in the form of a glucose oxidase immobilized membrane of the invention is formed on a base 101 and comprises an enzyme 102 in the form of glucose oxidase, gultaraldehyde 108, a material 107 in the form of bovine serum albumin adapted to cooperate with glutaraldehyde to form chemical crosslinking, and a water soluble photosensitive resin including polyvinyl pyrrolidone 109 and 2, 5-bis (4'-azide-2'-sulfobenzal) cyclopentanone sodium salt 110.

According to the present invention, an aqueous solution A containing glucose oxidase 102, the water soluble photosensitive resin and bovine serum albumin 107 is first coated on the surface of the base 101, and dried to provide a covering layer or membrane of which a specified portion is then irradiated by ultraviolet light 106 so as to form photo crosslinking therebetween, as pictured in FIG. 3A. Subsequently, the covering layer thus formed on the base 101 is developed by water to obtain a glucose oxidase immobilized membrane B (FIG. 3B) which is further treated by glutaraldehyde 108 to form chemical crosslinking for increased mechanical strength thereof.

Further, where the glucose oxidase immobilized membrane is formed on the entire surface of the base 1, it is preferable to use an aqueous solution containing glutaraldehyde of 10–25 weight percent. On the other hand, in the event that such a glucose-oxidase immobilized membrane is formed on only a specific portion of the base surface, ultraviolet light 6 is irradiated on only the specific portion of the base 1 and then developed by a 1–5% glutaraldehyde solution so as to form chemical crosslinking in the photo crosslinked portion thereof while dissolving the remaining portion thereof having no photo crosslinking for removal.

Figure 4:
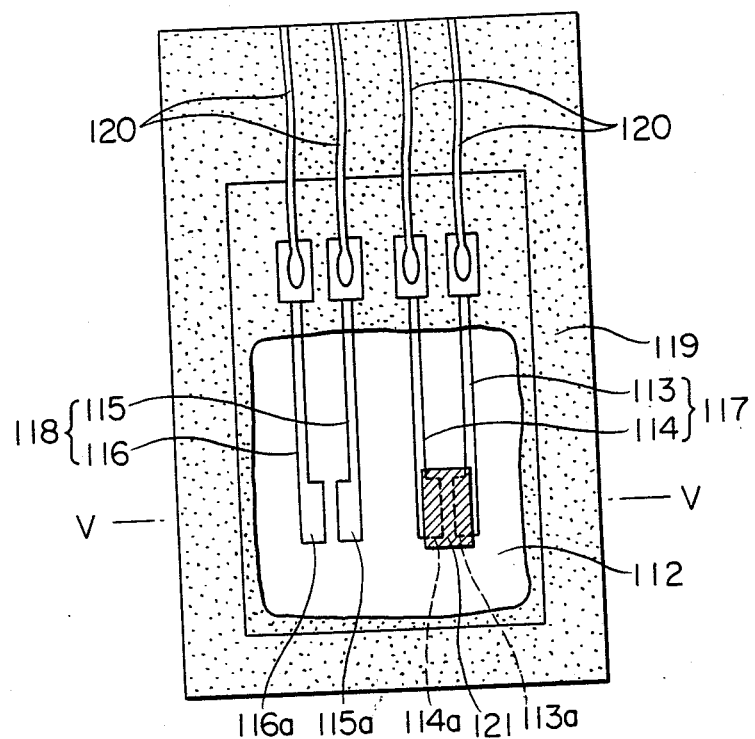
FIG. 4 is a partially cutaway plan view of a semiconductor enzyme sensor having a glucose oxidase immobilized membrane formed on a pH-ISFET in accordance with the present invention.
Figure 5:
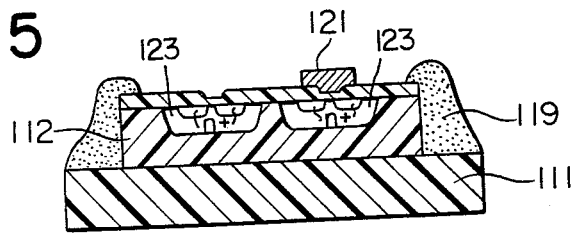
FIG. 5 is a cross sectional view taken along the line V—V in FIG. 4.

FIG. 4 and 5 show a semiconductor enzyme sensor which includes two pH-ISFETs having an enzyme immobilized membrane fabricated in accordance with the present invention. The sensor illustrated has a pH-ISFET chip or element 112 firmly or integrally mounted on an epoxy resin board 111 by means of an epoxy resin covering layer 119. The pH-ISFET chip 112 is provided on its one side surface with a first pH-ISFET 117 and a second pH-ISFET 118. The first pH-ISFET 117 has a first source electrode 113 and a first drain electrode 114 extending in a spaced parallel relation with each other, and the second pH-ISFET 118 has a second source electrode 115 and a second drain electrode 116 extending in a spaced parallel relation with each other. A pair of source and drain portions designated by n+ are formed in each of two p-well regions 123. These first and second source and drain electrodes 113 through 116 are electrically connected to a measuring circuit (not shown) via respective leads 120. The first pH-ISFET 117 has a portion between a pair of inwardly projected first spaced ion-sensitive portions 113a, 114a which are formed integrally with the first source and drain electrodes 113, 114 at their distal ends. An enzyme immobilized membrane 121 is formed on the first ion-sensitive portion between 113a, 114a of the first pH-ISFET 117 in accordance with the method of the invention as described in the foregoing with reference to FIGS. 3A through 3C. The second pH-ISFET 118 has second spaced ion-sensitive portion between a pair of inwardly projected portions 115a, 116a portion formed integrally with the second source and drain electrodes 115, 116 at their distal ends, the second ion-sensitive portions 115a, 116a being provided with no enzyme immobilized membrane and thus exposed outwards. Though not shown in FIGS. 4 and 5, a reference or pseude electrode such as, for example, a known silver-silver chloride electrode is usually required. In this manner, the semiconductor enzyme sensor is comprised of the first pH-ISFET 117 provided with the enzyme immobilized membrane 121. The second pH-ISFET 118 having no enzyme immobilized membrane, and the reference electrode (not shown).

Figure 6:
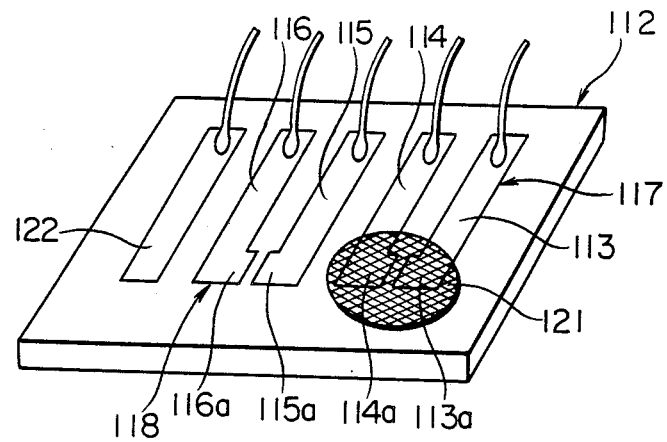
FIG. 6 is a perspective view of another semiconductor enzyme sensor in accordance with the present invention.
Figure 7:
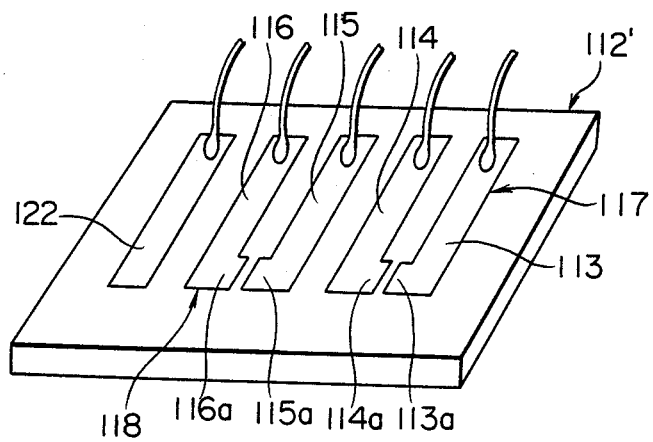
FIG. 7 is a perspective view showing a pH-ISFET chip having a plurality of substrate electrodes from which the semiconductor enzyme sensor of FIG. 6 is formed.

FIG. 6 shows another pH-ISFET chip or element 112' for a semiconductor enzyme sensor in accordance with the invention, and FIG. 7 shows the pH-ISFET chip without enzyme immobilized membrane. In these figures, the composite pH-ISFET chip 112' comprises a first pH-ISFET 117 including a first source electrode 113 and a first drain electrode 114, a second pH-ISFET 118 including a second source electrode 115 and a second drain electrode 116, and a reference or pseude electrode 122. The composite pH-ISFET chip 112 can be fabricated in accordance with a known method for producing a usual metallic oxide-semiconductor CMOS type field effect transistor. The first and second pH-ISFETs 117 and 118 are sensitive to hydrogen ions independently of each other so that they can measure the pH of a solution by measuring the current flowing between the source and drain electrodes 113 and 114 or 115 and 116 of the first or second pH-ISFET 117 or 118 when a predetermined voltage is applied between the source and drain electrodes, or alternately by measuring a source voltage required to be imposed between the source and drain electrodes for causing a predetermined level of current to flow across the source and drain electrodes. In this case, the source region was connected electrically to the p-well region 123. The first source and drain electrodes 113 and 114 of the first pH-ISFET 117 have an ion-sensitive portion between 113a and 114a which are integrally formed with their distal ends. Provided on a specified portion of the surface of the pH-ISFET chip 112 is a membrane 121 containing an immobilized enzyme, the ion concentration in the enzyme being adapted to change in accordance with the amount of reaction thereof with a substrate solution. The enzyme immobilized membrane 121 is secured to the surface of the pH-ISFET chip so as to cover the ion-sensitive portion between 113a and 114a of the first pH-ISFET. On the other hand, the second source and drain electrodes 115 and 116 of the second pH-ISFET 118 have no enzyme immobilized membrane connected therewith. With this arrangement, if a sample solution contains a substrate reactable with the enzyme in the membrane 121, there will be a difference in pH between the membrane and the solution which is monitored by means of the second pH-ISFET 118. Accordingly, the enzyme sensor acts to measure the respective source voltages required to cause a predetermined level of current flow from the sources 113, 115 to the drains 114, 116 of the first and second pH-ISFETs, and then amplify a differential output between the measured source voltages of the pH-ISFETs so as to measure the concentration of the substrate in the sample solution.

Figure 8:
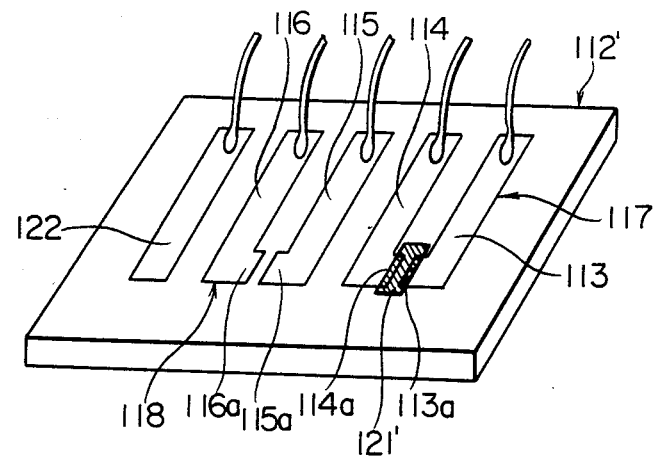
FIG. 8 is a perspective view showing a glucose sensor having a glucose oxidase immobilized membrane formed on only a portion of its ion-sensitive surface.

In addition, as illustrated in FIG. 8, it is possible to form an enzyme immobilized membrane 121' on a specified portion of the surface of a pH-ISFET chip by means of photolithography.

Figure 9:
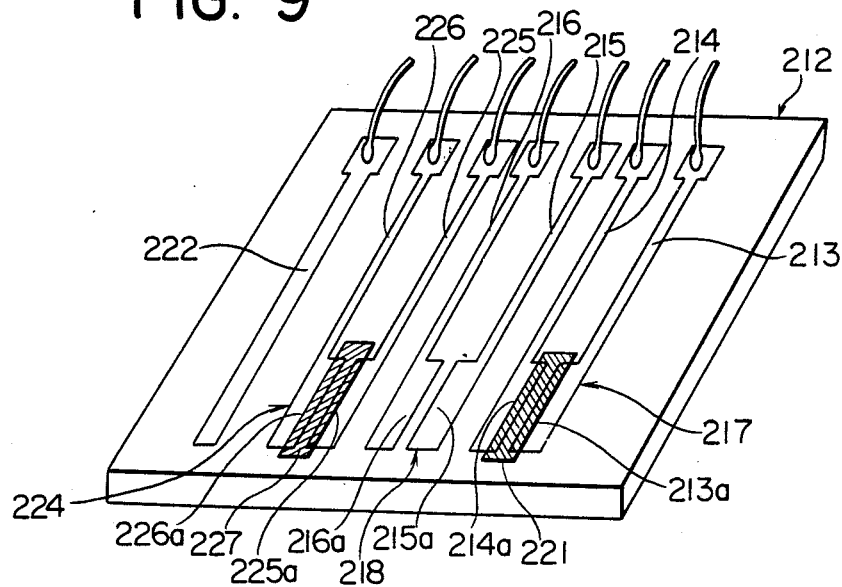
FIG. 9 is a perspective view of a multiple enzyme sensor in accordance with the present invention.

FIG. 9 shows a semiconductor multiple-enzyme sensor having a plurality (three in the illustrated embodiment) of pH-ISFETs 217, 218 and 224 each having a source electrode 213, 215 or 225 and a drain electrode 214, 216 or 226, and a reference or pseudo reference electrode 222 fabricated in accordance with the present invention. Each of the pH-ISFETs 217, 218 and 224 has an ion-sensitive portion between 213a, 214a; 215a, 216a; or between 225a, 226a which are integrally formed with the source and drain electrodes 213, 214; 215, 216; or 225, 226, respectively. The multiple-enzyme sensor has a plurality (two in the illustrated embodiment) of enzyme immobilized membranes 221, 227 which are formed on the ion-sensitive portion between 213a, 214a of the pH-ISFET 217, and on the ion-sensitive portion between 225a, 226a of the pH-ISFET 227, respectively. These enzyme immobilized membranes 221 and 227 can be formed in the same manner as described with reference to the one shown in FIGS. 4 and 5 or FIGS. 6 and 7. The membranes 221 and 227 are different from each other and reactable with different kinds of substrates so that they can measure concentrations of such different substrates in solutions. The multiple-enzyme sensor may further include one or more pH-ISFETs each having an enzyme reactable with a corresponding substrate.

EXAMPLE 1

An aqueous solution of a water soluble photosensitive polymer was prepared by dissolving 2, 5-bis (4'-azide-2'-sulfobenzal) cyclopentanone sodium salt (Tokyo Ohkakogyo Co., Ltd.) in a 10 weight percent polyvinyl pyrrodidone solution having a molecular weight of about three hundred and sixty thousand at a concentration of 10 weight percent. In 0.2 ml of the water soluble photosensitive polymer solution thus prepared, 2 mg glucose oxidase was dissolved as an enzyme to form a homogeneous solution which was then widely coated on a specific portion of the surface of the pH-ISFET chip 112, as illustrated in FIG. 6, so as to cover the ion-sensitive portion between 113a and 114a of the source and drain electrodes 113 and 114 of the first pH-ISFET 117 as well as a channel portion defined therebetween. The layer of the solution thus coated was made into an even or uniform membrane by the use of a spinner (not shown), and then dried. The dried membrane was subsequently exposed to UV irradiation with a 250 W superhigh voltage mercury-arc lamp for 2 minutes to form a glucose oxidase immobilized membrane 121.

EXAMPLE 2

To 0.2 ml of a 10 weight percent photosensitive polymer solution, which was prepared in the same manner as described in the Example 1, 20 mg glucose oxidase and 10 mg bovine serum albumin, which is a material adapted to form chemical crosslinking with glutaraldehyde, were added to form a homogeneous solution which was then coated on the ion-sensitive portions between 113a and 114a of the source and drain electrodes 113 and 114 of the first pH-ISFET 117 in FIG. 6. The layer of the solution thus coated was treated in the same manner as described in Example 1 to provide a glucose-oxidase immobilized membrane 121. Subsequently, the glucose-oxidase immobilized membrane 121 was immersed in a 25% glutaraldehyde solution for 10 minutes whereby protein molecules in the bovine serum albumin were chemically crosslinked with each other through chemical bondings for increased mechanical strength. The membrane thus treated was then washed with a buffer solution, immersed in a 0.1M glycine solution for 15 minutes for the purpose of removing the residual glutaraldehyde, and again washed with a buffer solution. In this manner, a glucose sensor having a glucose oxidase immobilized membrane was obtained.

Figure 10:
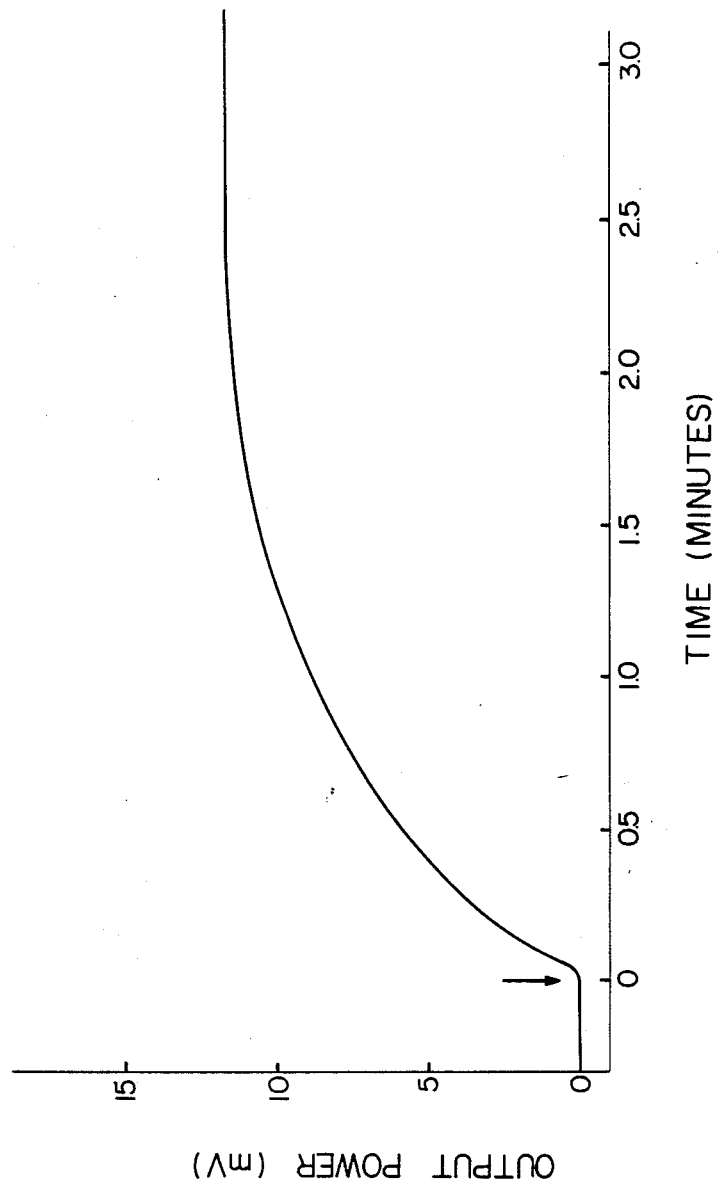
FIG. 10 is a graphic illustration showing a response characteristic of the glucose sensor of FIG. 8.
Figure 11:
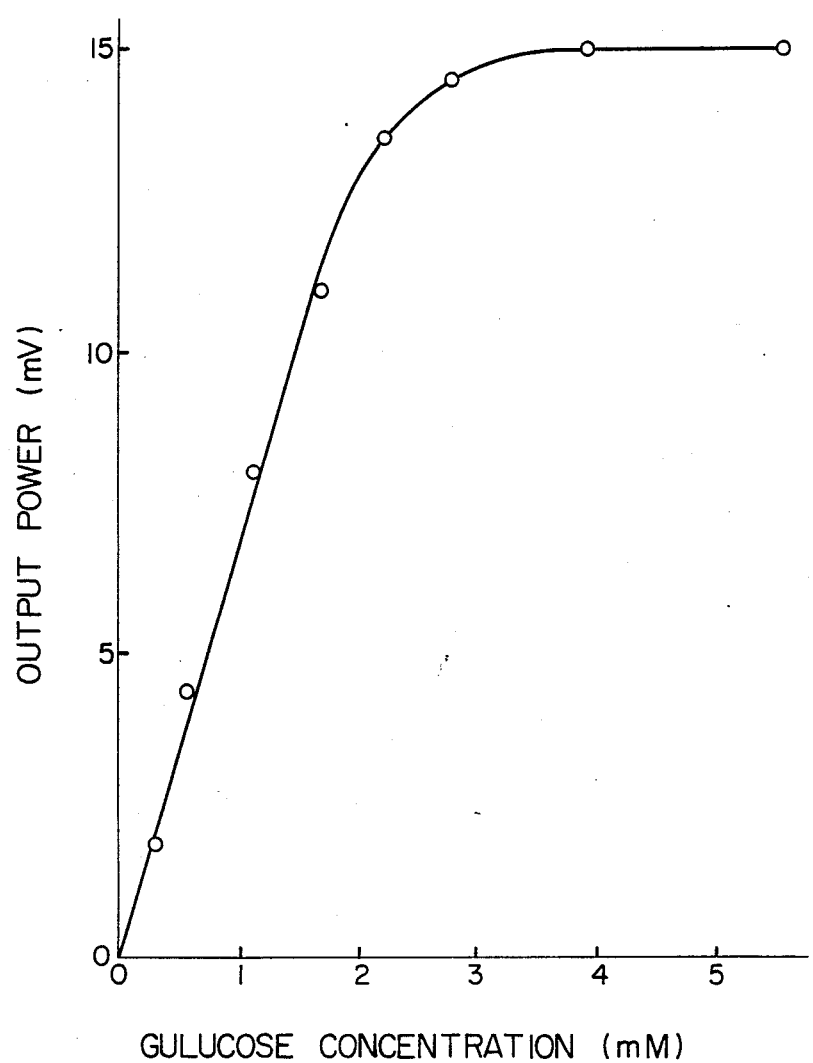
FIG. 11 is a graphic illustration showing a relationship between the output power and the glucose concentration in the glucose sensor of FIG. 8.

The glucose sensor thus fabricated was measured in terms of response characteristic. The measurements was carried out at a glucose concentration in the range of 0 to 5.5 mM using a 0.01M acetate buffer solution at pH 5.5. The response curve of the glucose sensor at a 1.67 mM glucose concentration is shown in FIG. 10 in which an arrow indicates a sample pouring point in time. From FIG. 10, it is clear that the response of the glucose sensor is fast. FIG. 11 shows a calibration curve of the glucose sensor from which it is seen that the sensor response is linear with respect to the glucose concentration in the range of 0 to 1.7 mM. In addition, the lifetime of the glucose sensor was 60 days, sufficiently long for practical use.

EXAMPLE 3

TO 0.2 ml of a 10 weight percent photosensitive polymer solution, which was prepared in the same manner as described in Example 1, 2 mg glucose oxidase was added to form a homogeneous solution which was then coated on the surface of the pH-ISFET chip 112' so as to cover the ion-sensitive portion between 113a and 114a of the source and drain electrodes 113 and 114 of the first pH-ISFET 117 in FIG. 8. The layer of the solution thus coated was made into an even or uniform membrane by the use of a spinner (not shown), and then dried. Thereafter, by using a photomask through which light is irradiated from a light source to a specified portion of the surface of pH-ISFET chip 112, a glucose oxidase immobilized enzyme membrane 121' was formed on only the ion-sensitive portion. The light irradiation was carried out with the same device and conditions as those in Example 1.

EXAMPLE 4

To 0.2 ml of a 10 weight percent photosensitive polymer solution, which was prepared in the same manner as described in the Example 1, 20 mg glucose oxidase and 10 mg bovine serum albumin were added to form a homogeneous solution which was then coated on the ion-sensitive portion between 113a and 114a of the source and drain electrodes 113 and 114 of the first pH-ISFET 117 in FIG. 8. The layer of the solution thus coated was made into a uniform membrane by the use of a spinner (not shown), and then dried. Thereafter, the membrane was treated in the same manner as described in Example 3 to provide a glucose oxidase immobilized membrane 121'. Subsequently, the glucose oxidase immobilized membrane was immersed in a 25% glutaraldehyde solution for 10 minutes whereby protein molecules in the bovine serum albumin were chemically crosslinked with each other through chemical bondings for increased mechanical strength. The glucose oxidase immobilized membrane thus treated was then washed with a buffer solution, immersed in a 0.1M glycine solution for 15 minutes for the purpose of removing the residual glutaraldehyde, and again washed with a buffer solution.

EXAMPLE 5

In 500 μl of a 10 weight percent photosensitive polymer solution, which was repeated in the same manner as described in the Example 1, 25 mg glucose oxidase and 25 mg bovine serum albumin were dissolved to form a homogeneous enzyme solution. The enzyme solution thus prepared was poured dropwise on the surface of a silicon wafer which has a thermally grown silicon oxide film of about 5000 Å thickness. The enzyme solution was then spin coated by a spinner (not shown) at 2000 rpm for 2 minutes to provide an enzyme membrane A, as illustrated in FIG. 3. After drying at room temperature, the enzyme membrane A was irradiated by ultraviolet light, of which less than 300 nm wavelengths were cut, through a photomask 105 for 180 seconds to form chemical crosslinking so as to provide an enzyme immobilized membrane B (see FIG. 3B). Subsequently, the enzyme immobilized membrane B thus obtained was developed by aqueous solutions containing glutaraldehyde of various concentrations, the aqueous solutions being adapted to form chemical bondings with glucose oxidase and bovine serum albumin. The pattern of the residual enzyme immobilized membrane C formed by the development was then observed and the results obanined were as follows:

(1) When developed with an aqueous solution containing a 0% concentration of glutaraldehyde, the largest portion of the membrane was peeled off and hence the membrane was poor.

(2) When developed with a 1% glutaraldehyde solution, the largest portion of the membrane was not peeled off and the membrane was good.

(3) When developed with a 2% glutaraldehyde solution, the membrane was not peeled off and very good.

(4) When developed with a 3% glutaraldehyde solution, the membrane was not peeled off and very good.

(5) When developed with a 4% glutaraldehyde solution, the membrane was not peeled off and very good.

(6) When developed with a 5% glutaraldehyde solution, the most portion of the membrane was not peeled off and good.

(7) When developed with a 10% glutaraldehyde solution, only half of the membrane pattern remained with a white thin film being formed due to chemical crosslinking at locations from which a half of the membrane pattern was peeled off.

(8) When developed with a 25% glutaraldehyde solution, the largest portion of the membrane portion was peeled off with a white thin film remaining due to chemical crosslinking.

From the above, it was found that with glutaraldehyde solutions at concentrations ranging from 1% to 5%, there were obtained good enzyme immobilized membranes.

EXAMPLE 6

An enzyme solution, prepared in the same manner as described in Example 5, was spin coated on the surface of a silicon wafer which has a thermally grown silicon oxide film of about 5000 Å thickness with amino groups being introduced on the surface thereof by using γ-aminopropyltriethoxysilane. The coating of the enzyme solution was effected by the use of a spinner (not shown) at 2000 rpm for 2 minutes to provide an enzyme membrane. The enzyme membrane was irradiated by ultraviolet light emitted from a 250 W superhigh voltage mercury-arc lamp, and then immersed in a 25% glutaraldehyde solution for 5 minutes. Thereafter, the unreacted aldehyde groups in the enzyme membrane were reacted with a 0.1M glycine solution for 15 minutes to provide a glucose oxidase immobilized membrane. The membrane thus obtanied had an average thickness of 2 μm and thus was of a very thin film though there were many irregularities formed on the surface thereof.

EXAMPLE 7

An enzyme solution, prepared in the same manner as described in Example 5, was spin coated on the surface of a silicon wafer which had a thermally grown silicon oxide film of about 5000 Å thickness with amino groups being introduced on the surface thereof by using γ-aminopropyltriethoxysilane. The coating of the enzyme solution was effected by a spinner (not shown) at 2000 rpm for 2 minutes to provide an enzyme membrane. Thereafter, by the use of a 250 W superhigh voltage mercury-arc lamp, ultraviolet light was irradiated through an appropriate photomask on a specified portion of the surface of a pH-ISFET chip so that only a portion of the enzyme membrane on the pH-ISFET chip surface was phote-set (see FIG. 3A). Subsequently, by dissolving and removing the unset portion of the enzyme membrane with distilled water, a glucose-oxidase immobilized enzyme membrane of a limited area was obtained (see FIG. 3B). The glucose oxidase immobilized membrane was then treated with a 25% glutaraldehyde solution for 5 minutes so as to form chemical crosslinking for increased mechanical strenth (see FIG. 3C). The membrane thus formed was immersed in a 0.1M glycine solution for 15 minutes for reaction of the unreacted aldehyde groups in the glutaraldehyde.

EXAMPLE 8

An enzyme solution, prepared in the same manner as described in Example 5, was coated on the surface of a silicon wafer which has a thermally grown silicon oxide film of about 5000 Å thickness with amino groups being introduced on the surface thereof by using γ-aminopropyltriethoxysilane, as in Example 6. The enzyme solution was then spin coated by a spinner (not shown) at 2000 rpm for 2 minutes to provide an enzyme membrane A in FIG. 3A. Subsequently, only a specified portion of the enzyme membrane A was irradiated by ultaviolet light emitted from a 250 W superhigh voltage mercury-arc lamp through an appropriate photomask so as to be photo-set (FIG. 3A). The silicon wafer with the photo-set enzyme membrane was then immersed in a 2% glutaraldehyde solution whereby the unset portion B of the membrane was dissolved for removal, as shown FIG. 3B, and at the same time, chemical crosslinking was formed in the photo-set portion of the membrane to provide a glucose-oxidase immobilized membrane C of a limited area (FIG. 3C). To remove the unreacted aldehyde groups in the glucose oxidase membrane it was immersed in a 0.1M glycine solution for 15 minutes for reaction therewith. It was possible to reduce the size of the glucose oxidase immobilized enzyme membrane thus obtained such that it had a line and space pattern with a pitch or interval of 100 μm between adjacent lines or spaces,.

EXAMPLE 9

A silicon wafer was processed in the same manner as in Example 8, and after being developed with a 2% glutaraldehyde solution, it was immersed in a 25% glutaraldehyde solution for 5 minutes so that further chemical crosslinking was produced in an enzyme membrane once chemically crosslinked for further increase in mechanical strength to provide a glucose oxidase immobilized membrane.

Here, it is to be noted that though in Examples 6 through 9 above, pH-ISFETs each in the form of a silicon wafer having amino groups introduced into the surface thereof were used, the present invention can be likewise applicable to a transducer.

EXAMPLE 10

A first enzyme immobilized membrane was formed on a hydrogen ion-sensitive portion of a pH-ISFET in the same manner as in Example 5 so as to provide a test piece of a semiconductor enzyme sensor of the invention. On the other hand, using an enzyme solution prepared in the same manner as in Example 5 excepting that there was no addition to bovine serum albumin, a comparative semiconductor enzyme sensor was produced which had a second enzyme immobilized membrane formed on a hydrogen ion-sensitive portion of another pH-ISFET in the same manner as in Example 5. The operations of the above two sensors were examined in the following manner. In case of the comparative sensor in which photo crosslinking was formed by the use of a water soluble photosensitive polymer containing the enzyme alone but no bovine serum albumin, the membrane produced was peeled off in an aqueous solution and hence there was no enzyme immobilized membrane formed. Presumably, this was caused by too large an amount of enzyme contained. In contrast to this, in the test piece of the sensor produced by using bovine serum albumin, there was no peeling off of the membrane even in an aqueous solution, and thus an enzyme immobilized membrane having sufficient mechanical strength was obtained. The response of this sensor to a 300 mg/l in a 10 mM acetate buffer solution was approximately 6 mV at pH 5.5 and 34° C., and the sensor had high sensitivity.

Although in this Example, the semiconductor enzyme sensor having a pH-ISFET is described, the present invention is likewise applicable to a semiconductor oxygen sensor, a semiconductor hydrogen peroxide sensor, or the like with the same effects.

EXAMPLE 11

A multiple-enzyme sensor was produced in which an enzyme in the form of glucose oxidase and another enzyme in the form of lipase were used for simultaneously detecting glucose and neutral lipids,. 2 mg lipase was dissolved in 0.2 ml of a water soluble photosensitive solution as prepared in the same manner as in Example 1. The solution thus formed was coated on a pH-ISFET chip by means of a spinner (not shown) and dried to provide a membrane which was then irradiated by light emitted from an exposure device through an appropriate photomask for 1 minute so as to photo-set only a portion of the membrane. Subsequently, the remaining portion of the membrane (or mixture of the enzyme and the water soluble photosensitive resin) other than the photo-set portion was dissolved in a buffer solution for removal. On the other hand, glucose oxidase was subjected to the same processes as described above with respect to lipase so as to provide a glucose oxidase immobilized membrane which was secured to a portion of the pH-ISFET chip.

EXAMPLE 12

15 mg lipase and 10 mg bovine serum albumin were dissolved in a 0.2 ml water soluble photosensitive resin solution as prepared in the same manner as in Example 1. The solution thus formed was coated on the surface of a pH-ISFET by means of a spinner and dried to provide a membrane. Only a portion of the membrane was exposed to irradiation of ultraviolet light for 2 minutes so as to be photo-set to provide a lipase immobilized membrane. The remaining portion of the membrane other than the photo-set portion was dissolved and removed by an aqueous solution. On the other hand, a water soluble photosensitive resin solution containing glucose oxidase, similar in composition to that in Example 2, was subjected to the same processes as in the above-described water soluble photosensitive resin solution so as to form a glucose oxidase immobilized membrane on a specific portion of the surface of the pH-ISFET chip. Subsequently, both of the enzyme immobilized membranes thus obtained were immersed in a 25% glutaraldehyde solution for 10 minutes so that the proteins in the enzyme immobilized membrane were crosslinked with each other through chemical bondings. After being washed with a buffer solution, the enzyme immobilized membranes were further immersed in a 0.1M glycine for removal of the residual glutaraldehyde, and then washed again with a buffer solution. In this manner, a multiple-enzyme sensor was produced.

The multiple-enzyme sensor thus produced was examined in terms of response characteristic. FIG. 12 illustrates an example of the output power of the sensor in which a sample pouring point in time is designated by an arrow. The output power of the sensor examined was measured by using a 2 mM tris-maleate acid buffer solution (pH 7) containing 1.67 mM glucose and 3 mM triolein. In FIG. 12, curve A represents a differential output between the pH-ISFET having a lipase immobilized membrane and the pH-ISFET without any enzyme immobilized membrane. Triolein was hydrolyzed into oleic acid according to the following reaction (2) to provide the output curve A.

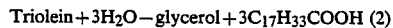

$$\text{Triolein} + 3H_2O \rightarrow \text{glycerol} + 3C_{17}H_{33}COOH \quad (2)$$

On the other hand, curve B in FIG. 12 represents a differential output between the pH-ISFET having a glucose oxidase immobilized membrane and the pH-ISFET without any enzyme immobilized membrane. Glucose was changed to gluconic acid, as shown in the above reaction (1), so that pH of the enzyme immobilized membrane was accordingly reduced to provide the output curve B. The measurement by the multiple sensor was possible in a glucose concentration ranging from 0 to 3 mM and at a triolein concentration ranging from 0 to 4 mM.

Although in this example, a pseudo reference electrode in the form of a thin membrane of a novel metal was used to provide gate voltage, a table reference electrode such as a silver-silver chloride electrode may be employed. Also, glucose oxidase and lipase were used for enzymes, but instead by the use of other kinds of enzymes, it is possible to produce a semiconductor sensor or a multiple-enzyme sensor, which is sensitive to various substrates.

Although in the above-described examples the mixture of PVP and bis-azide compound is used for a water soluble photosensitive resin, there may be employed with the same effects other types of water soluble photosensitive resins such as photosensitive polyvinyl alcohols each having, as a pendant, a stilbazolium group. Further, enzymes are not limited to glucose oxidase or lipase but other kinds of enzymes such as urease can be used. Moreover, in place of a combination of bovine serum albumin and an enzyme with glutaraldehyde, there may be employed any combination of general reagents which are usable with water soluble immobilized enzymes which are able to easily from chemical crosslinking therewith. For example, poly-L-lysine or copolymers of polyamino acid and poly-L-lysine can be used in place of bovine serum albumin, and a polyfunctional reagent having a plurality of aldehyde groups can be used in place of glutaraldehyde.

What is claimed is:

1. A membrane containing an immobilized enzyme comprising:
    a water soluble photosensitive resin including polyvinyl pyrrolidone having a high molecular weight crosslinked to 2, 5-bis (4'-azide2'-sulfobenzal) cyclopentanone sodium salt; and an enzyme.

2. A membrane as set forth in claim 1 wherein said enzyme is selected from the group consisting of glucose oxidase, urease and lipase.

3. A membrane as set forth in claim 1, further comprising;
glutaraldehyde; and
a material adapted to cooperate with glutaraldehyde to form chemical crosslinking.

4. A membrane as set forth in claim 3 wherein said enzyme is selected from the group consisting of glucose oxidase, urease and lipase.

5. A membrane as set forth in claim 3 wherein said material adapted to cooperate with glutaraldehyde to form chemical crosslinking is selected from the group consisting of bovine serum albumin, polyamino acid, and polyamino acid copolymer.

6. A membrane as set forth in claim 4 wherein said material adapted to cooperate with glutaraldehyde to form chemical crosslinking is selected from the group consisting of bovine serum albumin, polyamino acid, and polyamino acid copolymer.

7. A membrane as set forth in claim 5 wherein said polyamino acid is poly-L-lysine.

8. A membrane as set forth in claim 6 wherein said polyamino acid is poly-L-lysine.

9. A membrane as set forth in claim 5 wherein said polyamino acid copolymer is a copolymer of poly-L-lysine and poly-L-thyrosin.

10. A membrane as set forth in claim 6 wherein said polyamino acid copolymer is a copolymer of poly-L-lysine and poly-L-thyrosin.

11. A membrane as set forth in claim 1 wherein said polyvinyl pyrrolidone having a high molecular weight is 2–20 weight %; and said 2, 5-bis (4'-azide-2'-sulfobenzal) cyclopentanone sodium salt is 0.5–1.5 weight %; and said enzyme comprises glucose oxidase of 5.0–7.5 weight %; said membrane further comprising bovine serum albumin of 5–10 weight %.

12. A method for producing a membrane containing an immobilized enzyme comprising the steps of:
coating on a base an aqueous solution which is composed of a water soluble photosensitive resin including polyvinyl pyrrolidone having a high molecular weight and 2,5-bis(4'-azide-2'-sulfobenzal) cyclopentanone sodium salt, and an enzyme;
drying the aqueous solution thus coated on said base so as to form a membrane containing an immobilized enzyme; and
irradiating said membrane containing an immobilized enzyme with ultraviolet light to provide photocrosslinking between said polyvinyl pyrrolidone, said cyclopentanone sodium salt, and said enzyme.

13. A method for producing a membrane as set forth in claim 12 wherein said enzyme is selected from the group consisting of glucose oxidase, urease and lipase.

14. A method for producing a membrane as set forth in claim 12 wherein said aqueous solution further comprises;
glutaraldehyde; and
a material adapted to cooperate with glutaraldehyde to form chemical crosslinking.

15. A method for producing a membrane as set forth in claim 14 wherein said enzyme is selected from the group consisting of glucose oxidase, urease and lipase.

16. A method for producing a membrane as set forth in claim 14 wherein said material adapted to cooperate with glutaraldehyde to form chemical crosslinking is selected from the group consisting of bovine serum albumin, polyamino acid, and polyamino acid copolymer.

17. A method for producing a membrane as set forth in claim 15 wherein said material adapted to cooperate with glutaraldehyde to form chemical crosslinking is selected from the group consisting of bovine serum albumin, polyamino acid, and polyamino acid copolymer.

18. A method for producing a membrane as set forth in claim 16 wherein said polyamino acid is poly-L-lysine.

19. A method for producing a membrane as set forth in claim 17 wherein said polyamino acid is poly-L-lysine.

20. A method for producing a membrane as set forth in claim 16 wherein said polyamino acid copolymer is a copolymer of poly-L-lysine and poly-L-thyrosin.

21. A method for producing a membrane as set forth in claim 17 wherein said polyamino acid copolymer is a copolymer of poly-L-lysine and poly-L-thyrosin.

22. A method for producing a membrane as set forth in claim 12 wherein said polyvinyl pyrrolidone having a high molecular weight is 2–20 weight %; and said 2, 5-bis (4'-azide-2'-sulfobenzal) cyclopentanone sodium salt is 0.5–1.5 weight %; and said enzyme comprises glucose oxidase of 5.0–7.5 weight %; said aqueous solution further comprising bovine serum albumin of 5–10 weight %.

23. A method for producing a membrane as set forth in claim 12 further comprising dipping said membrane after irradiation by said ultraviolet light into an aqueous solution of glutaraldehyde so as to form chemical crosslinking.

24. A method for producing a membrane as set forth in claim 23 further comprising washing the membrane containing an immobilized enzyme with a buffer solution after crosslinking.

25. A method for producing a membrane as set forth in claim 24 wherein said enzyme immobilized in said membrane is glucose oxidase.

26. A method for producing a membrane as set forth in claim 24 further comprising:
dipping said membrane containing an immobilized enzyme into an aqueous solution of glycine after washing with said buffer solution; and
again washing said membrane containing an immobilized enzyme with a buffer solution for removal of residual glutaraldehyde.

27. A method for producing a membrane as set forth in claim 26 wherein said enzyme immobilized in said membrane is glucose oxidase.

28. A sensor containing an enzyme comprising:
a first pH-ion sensitive field effect transistor having a membrane containing a first immobilized enzyme, said membrane being composed of a first water soluble photosensitive resin including polyvinyl pyrrolidone having a high molecular weight crosslinked to 2,5-bis(4'-azide-2'-sulfobenzal) cyclopentanone sodium salt, and said first enzyme;
a second pH-ion sensitive field effect transistor; and
a reference electrode.

29. A sensor containing an enzyme as set forth in claim 28 further comprising a third pH-ion sensitive field effect transistor having a membrane containing a second immobilized enzyme deposited thereon, said second membrane being composed of a second water soluble photosensitive resin including polyvinyl pyrrolidone having a high molecular weight of and 2,5-bis(4'-azide-2'-sulfobenzal) cyclopentanone sodium salt, and said second enzyme.

30. A sensor containing an enzyme as set forth in claim 28 wherein said first enzyme is selected from the group consisting of glucose oxidase, urease and lipase.

31. A sensor containing an enzyme as set forth in claim 29 wherein said second enzyme is selected from the group consisting of glucose oxidase, urease and lipase.

32. A sensor containing an enzyme as set forth in claim 28 further comprising;
glutaraldehyde; and
a material adapted to cooperate with glutaraldehyde to form chemical crosslinking.

33. A sensor containing an enzyme as set forth in claim 29 further comprising;
glutaraldehyde; and
a material adapted to cooperate with glutaraldehyde to form chemical crosslinking.

34. A sensor containing an enzyme as set forth in claim 31 wherein said first enzyme is selected from the group consisting of glucose oxidase, urease and lipase.

35. A sensor containing an enzyme as set forth in claim 32 wherein said second enzyme is selected from the group consisting of glucose oxidase, urease and lipase.

36. A sensor containing an enzyme as set forth in claim 32 wherein said material adapted to cooperate with glutaraldehyde to form chemical crosslinking in selected from the group consisting of bovine serum albumin, polyamino acid, and polyamino acid copolymer.

37. A sensor containing an enzyme as set forth in claim 33 wherein said material adapted to cooperate with glutaraldehyde to form chemical crosslinking is selected from the group consisting of bovine serum albumin, polyamino acid, and polyamino acid copolymer.

38. A sensor containing an enzyme as set forth in claim 34 wherein said material adapted to cooperate with glutaraldehyde to form chemical crosslinking is selected from the group consisting of bovine serum albumin, polyamino acid, and polyamino acid copolymer.

39. A sensor containing an enzyme as set forth in claim 35 wherein said material adapted to cooperate with glutaraldehyde to form chemical crosslinking is selected from the group consisting of bovine serum albumin, polyamino acid, and polyamino acid copolymer.

40. A sensor containing an enzyme as set forth in claim 36 wherein said polyamino acid is poly-L-lysine.

41. A sensor containing an enzyme as set forth in claim 37 wherein said polyamino acid is poly-L-lysine.

42. A sensor containing an enzyme as set forth in claim 38 wherein said polyamino acid is poly-L-lysine.

43. A sensor containing an enzyme as set forth in claim 39, wherein said polyamino acid is poly-L-lysine.

44. A sensor containing an enzyme as set forth in claim 36 wherein said polyamino acid copolymer is a copolymer of poly-L-lysine and poly-L-thyrosine.

45. A semiconductor enzyme sensor as set forth in claim 37 wherein said polyamino acid copolymer is a copolymer of poly-L-lysine and poly-L-thyrosine.

46. A sensor containing an enzyme as set forth in claim 38 wherein said polyamino acid copolymer is a copolymer of poly-L-lysine and poly-L-thyrosine.

47. A sensor containing an enzyme as set forth in claim 39 wherein said polyamino acid copolymer is a copolymer of poly-L-lysine and poly-L-thyrosine.

48. A sensor containing an enzyme as set forth in claim 28 wherein said polyvinyl pyrrolidone having a high molecular weight is 2–20 weight %; and said 2,5-bis (4'-azide-2'-sulfobenzal) cyclopentanone sodium salt is 0.5–1.5 weight %; and said enzyme comprises glucose oxidase of 5.0–7.5 weight %; said membrane containing a first immobilized enzyme further comprising bovine serum albumin of 5–10 weight %.

49. A sensor containing an enzyme as set forth in claim 29 wherein said polyvinyl pyrrolidone having a high molecular weight is 2–20 weight %; and said 2, 5-bis (4'-azide-2'-sulfobenzal) cyclopentanone sodium salt is 0.5–1.5 weight %; and said enzyme comprises glucose oxidase of 5.0–7.5 weight %; said membrane containing a second immobilized enzyme further comprising bovine serum albumin of 5–10 weight %.

50. A sensor containing an enzyme as set forth in claim 28 wherein said membrane containing a first immobilized enzyme is directly coated and hardened on said pH-ion sensitive field effect transistor.

51. A sensor containing an enzyme as set forth in claim 29 wherein said membrane containing a second immobilized enzyme is directly coated and hardened on said pH-ion sensitive field effect transistor.

52. A sensor containing an enzyme as set forth in claim 28 wherein said membrane containing a first immobilized enzyme is formed by coating on a pH-ion sensitive field effect transistor a first aqueous solution containing said first water soluble photosensitive resin, glucose oxidase, bovine serum albumin, and hardening said first aqueous solution thus coated by irradiation with ultraviolet light, said membrane containing a first immobilized enzyme being dipped into a glutaraldehyde solution to form chemical crosslinking for improved mechanical strength.

53. A sensor containing an enzyme as set forth in claim 29 wherein said membrane containing a second immobilized enzyme is formed by coating on a pH-ion sensitive field effect transistor a second aqueous solution containing said second water soluble photosensitive resin, glucose oxidase, bovine serum albumin, and hardening said second aqueous solution thus coated by irradiation with ultraviolet light, said membrane containing a second immobilized enzyme being dipped into a glutaraldehyde solution to form chemical crosslinking for improved mechanical strength.

54. A sensor containing an enzyme as set forth in claim 28 wherein said first pH-ion sensitive field effect transistor has an ionsensitive surface, and said membrane containing a first immobilized enzyme is formed through patterning on the ion-sensitive surface of said first pH-ion sensitive field effect transistor by means of photolithography.

55. A sensor containing an enzyme as set forth in claim 29 wherein said third pH-ion sensitive field effect transistor has an ion-sensitive surface, and said membrane containing a second immobilized enzyme is formed through patterning on the ion-sensitive surface of said third pH-ion sensitive field effect transistor by means of photolithography.

56. A sensor containing an enzyme as set forth in claim 28 further comprising one or more pH-ion sensitive field effect transistors each having a further membrane containing an immobilized enzyme connected thereto, said further membrane being composed of a further water soluble photosensitive resin including polyvinyl pyrrolidone having a high molecular weight crosslinked to 2, 5-bis (4'-azide-2'-sulfobenzal) cyclopentanone sodium salt, and a further enzyme.

* * * * *